(12) United States Patent
Manushakian

(10) Patent No.: US 6,355,035 B1
(45) Date of Patent: Mar. 12, 2002

(54) SURGICAL CUTTING TOOL

(75) Inventor: Hagop Samuel Manushakian, London (GB)

(73) Assignee: Martin Christopher Weisselberg, London (GB)

( * ) Notice: Subject to any disclaimer, the term of this patent is extended or adjusted under 35 U.S.C. 154(b) by 0 days.

(21) Appl. No.: 09/160,380

(22) Filed: Sep. 25, 1998

Related U.S. Application Data

(63) Continuation-in-part of application No. 08/737,551, filed as application No. PCT/GB95/01088 on May 12, 1995, now Pat. No. 5,833,703.

(30) Foreign Application Priority Data

May 14, 1994 (GB) ............................................. 9409625

(51) Int. Cl.⁷ ............................................... A61B 17/39
(52) U.S. Cl. ............................ 606/50; 606/45; 606/174
(58) Field of Search ............................... 606/1, 39, 45, 606/50–52, 174, 46, 48, 37; 30/140

(56) References Cited

U.S. PATENT DOCUMENTS

| | | | |
|---|---|---|---|
| 2,751,908 A | 6/1956 | Wallace | |
| 3,651,811 A | 3/1972 | Hildebrandt et al. | |
| 3,807,406 A | 4/1974 | Rafferty et al. | |
| 4,049,002 A | 9/1977 | Kletschka et al. | |
| 4,375,218 A | 3/1983 | Digeronimo | |
| 4,960,419 A | 10/1990 | Rosenberg | |
| 5,046,251 A | * 9/1991 | Scott | |
| 5,071,418 A | 12/1991 | Rosenbaum | |
| 5,116,332 A | * 5/1992 | Lottick | 606/52 |
| 5,324,289 A | * 6/1994 | Eggers | |
| 5,496,312 A | * 3/1996 | Klicek | 606/51 |
| 5,573,534 A | * 11/1996 | Stone | 606/48 |
| 5,658,281 A | * 8/1997 | Heard | |
| 5,827,281 A | * 10/1998 | Levin | 606/52 |
| 5,921,984 A | * 7/1999 | Sutcu et al. | |
| 6,024,744 A | * 2/2000 | Kese et al. | 606/51 |

FOREIGN PATENT DOCUMENTS

| | | |
|---|---|---|
| EP | 0 572 131 | 12/1993 |
| FR | 2 143 091 | 2/1973 |

* cited by examiner

Primary Examiner—David O. Reip
Assistant Examiner—William Lewis
(74) Attorney, Agent, or Firm—McDermott, Will & Emery

(57) ABSTRACT

A surgical cutting tool which is provided with means enabling suction to be applied to the site of operation of the tool. The tool may for example be a pair of surgical scissors or a surgical scalpel. The tool may be provided with a mechanism for effecting cauterization, and/or clamping tissue on which the surgeon is operating.

10 Claims, 8 Drawing Sheets

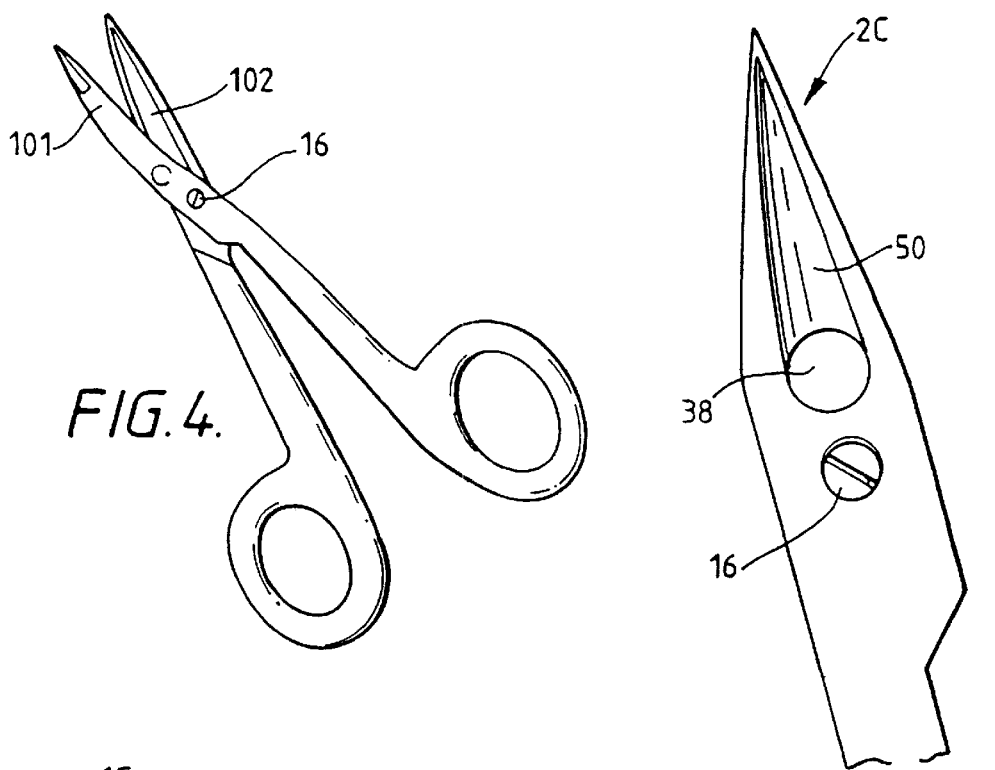
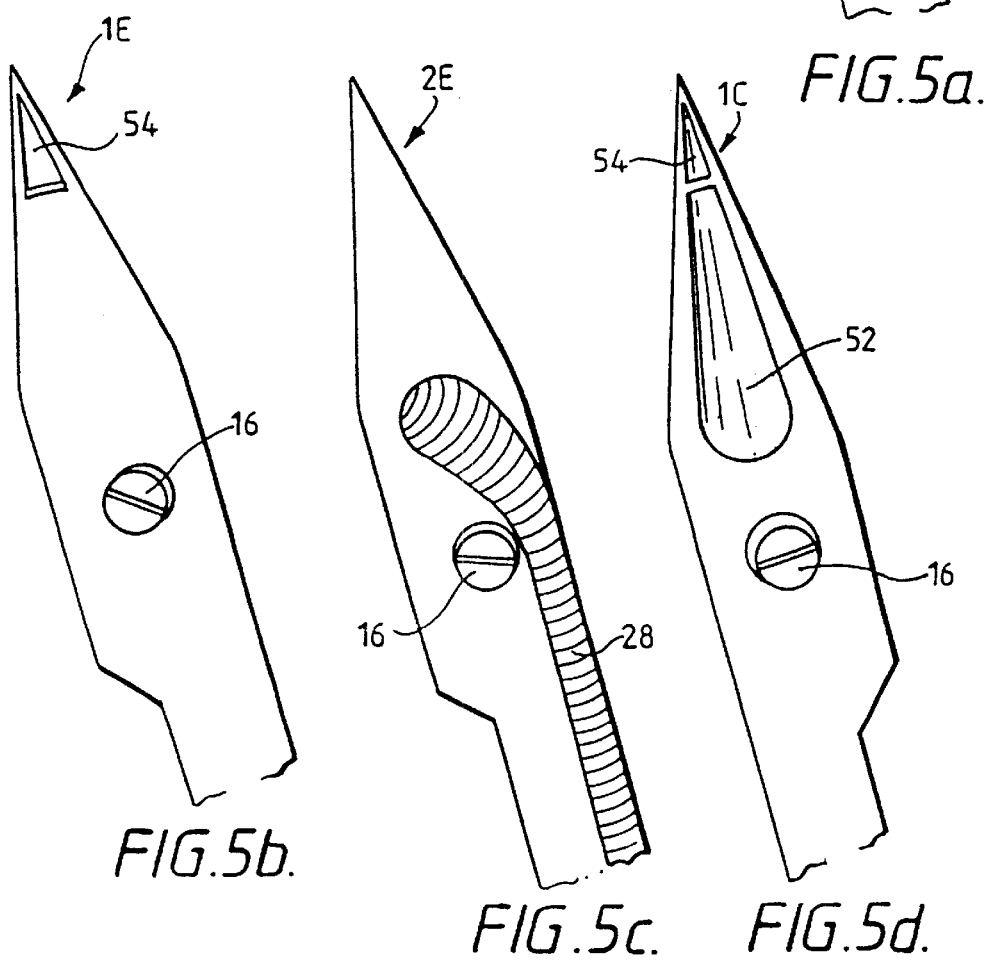

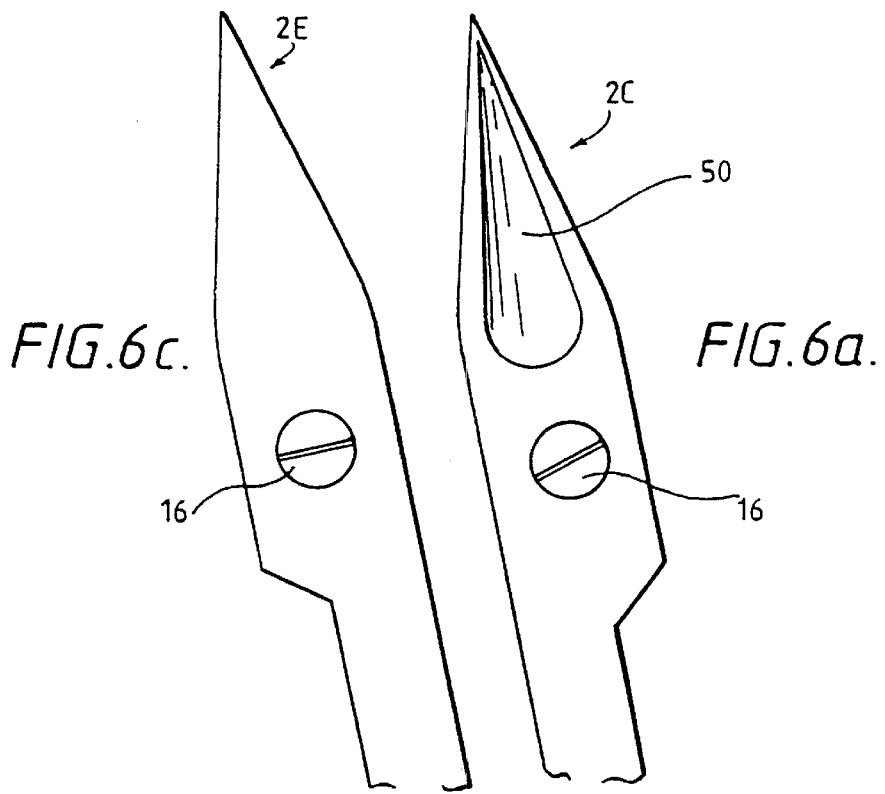
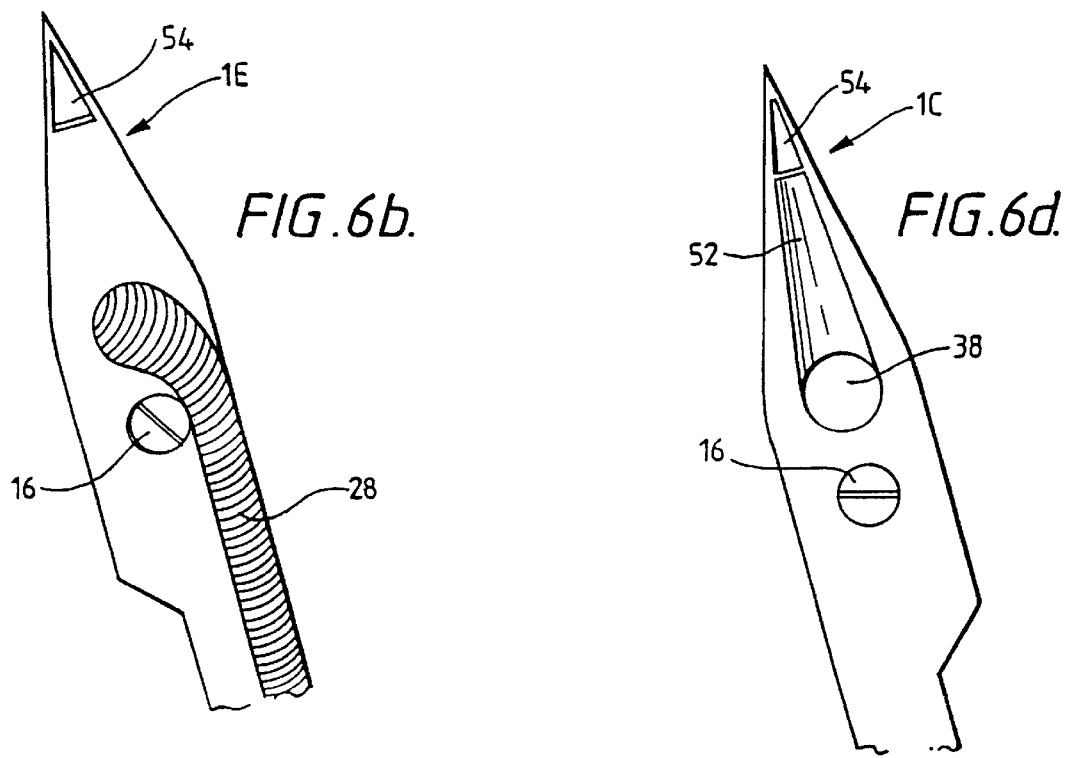

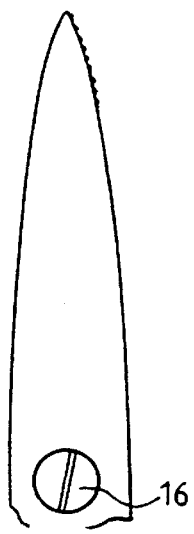 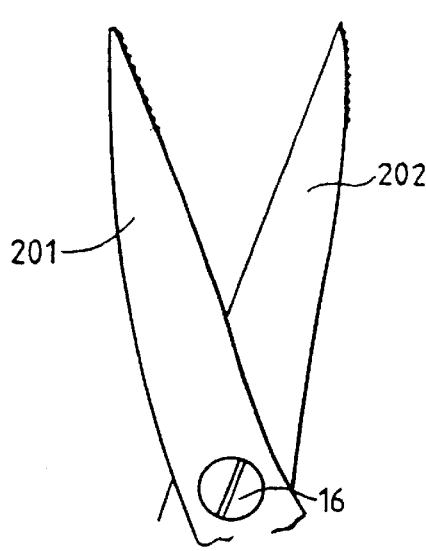 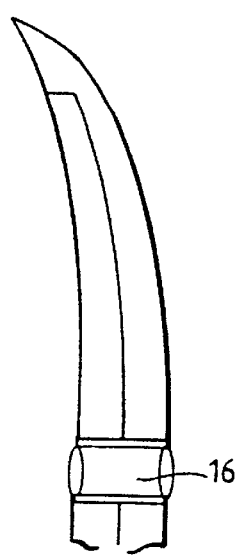
FIG 7a.    FIG.7b.    FIG.7c.
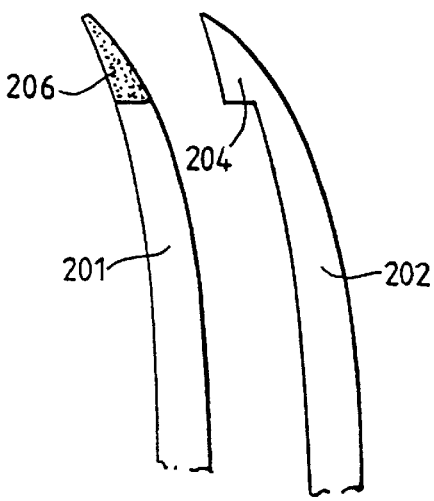 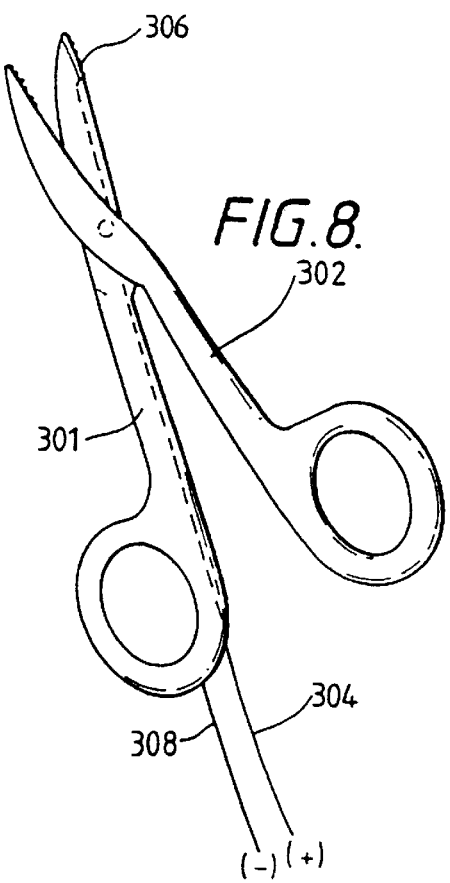
FIG.7d.    FIG.8.

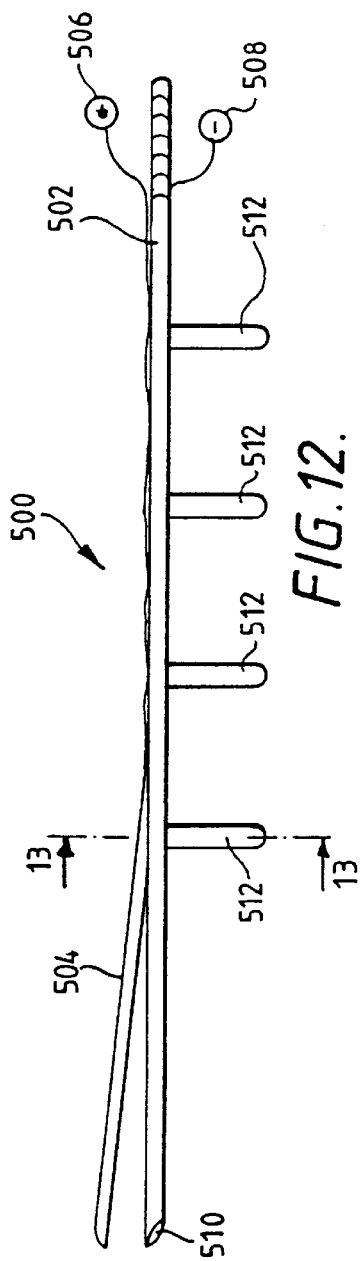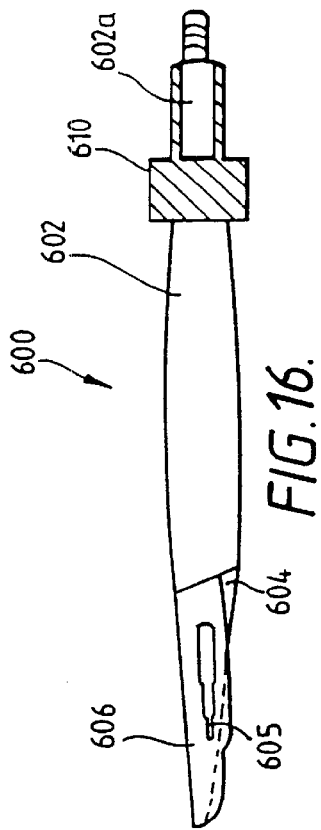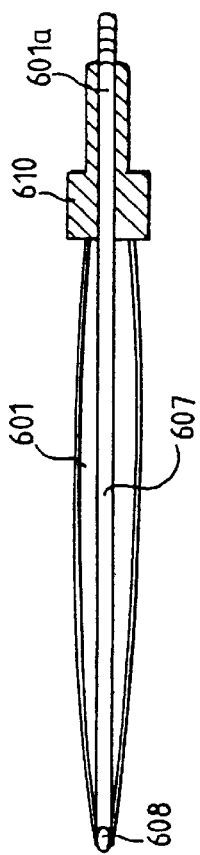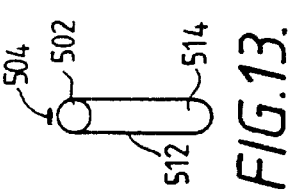

SURGICAL CUTTING TOOL

RELATED APPLICATION

This application is a continuation-in-part of U.S. Ser. No. 08/737,551 filed Mar. 14, 1997, now U.S. Pat. No. 5,833, 703, which is a 371 of PCT/GB95/01088, filed May 12, 1995.

BACKGROUND OF THE INVENTION

This invention relates to a surgical cutting tool.

When using such a tool, for example surgical scissors, or a surgical scalpel, the surgeon normally needs to have at least one assistant who can carry out suctioning at the site where the surgical tool is being used, so as to remove blood and other body fluids which are released by the use of the tool and which would otherwise obscure the surgeon's field of view. Such an assistant may also carry out ancillary tasks, for example cauterization.

However, the need to involve an assistant has a number of disadvantages. One of these is that the carrying out of activities by the assistant at the same site as that where the surgeon is working may impede the surgeon's activities, and thus render them more difficult, or at least make the operation more lengthy. Furthermore, if it were not necessary for the assistant to carry out suctioning and cauterization, the assistant might be more usefully employed in other tasks to assist the surgeon, and under some circumstances no assistant might be required at all.

SUMMARY OF THE INVENTION

According to one aspect of the present invention there is provided a pair of surgical scissors comprising first and second blades each having a cutting surface and an exterior surface, the cutting surfaces facing one another, the blades being pivotally connected to one another for relative pivotal movement about a pivotal axis, one of the blades having a blade portion located distally of the pivot axis and electrically insulated from the remainder of the blade, a first electrical conductor electrically connected to the said blade portion, and a second electrical conductor electrically connected elsewhere on the scissors, thereby enabling the scissors to act as a cautery.

According to another aspect of the invention there is provided a surgical tool in the form of a combined forceps/ scalpel unit, which comprises first and second forceps arms movable towards one another, each arm having interior surfaces facing towards one another and exterior surfaces facing away from one another, a mounting for enabling a scalpel blade to be mounted on the exterior surface of one of the arms, and suction means for enabling suction to be applied to the site of operation of the tool.

According to yet another aspect of the invention there is provided a surgical tool in the form of a combined forceps/ scalpel unit, which comprises first and second forceps arms movable towards one another, each arm having interior surfaces facing towards one another and exterior surfaces facing away from one another, a mounting for enabling a scalpel blade to be mounted on the exterior surface of one of the arms, and electrical connections to both forceps arms to enable the tool to act as a bipolar cautery.

The surgical cutting tool according to the invention may be provided with means for clamping tissue on which the surgeon is operating.

Other aspects of the invention will appear from the following description and claims.

The invention will now be further described with reference to the accompanying drawings.

BRIEF DESCRIPTION OF THE DRAWINGS

FIG. 4 shows a second embodiment of surgical scissors according to the invention;

FIGS. 5a to 5d show a first combination of scissor tip configurations which can be used in the scissors of FIG. 4;

FIGS. 6a to 6d show a second combination of tip configurations which can be used in the scissors of FIG. 4;

FIGS. 7a to 7d show the incorporation of a clamp in a pair of surgical scissors, and are respectively a plan view with the scissors closed, a plan view with the scissors open, a side view with the scissors closed, and a side view with the blades separated for the sake of clarity, to show their construction;

FIG. 8 shows a pair of scissors incorporating means for cauterization;

FIG. 12 is a side view of a suction/cautery unit provided with means for removably receiving a scalpel;

FIG. 13 is a section taken on line 13—13 in FIG. 12;

FIG. 16 shows the forceps in the view of FIG. 15, but with a blade in position;

FIG. 17 shows the forceps in a view at 180° to that of FIG. 15; and

DETAILED DESCRIPTION OF THE PREFERRED EMBODIMENTS

Figure 1:
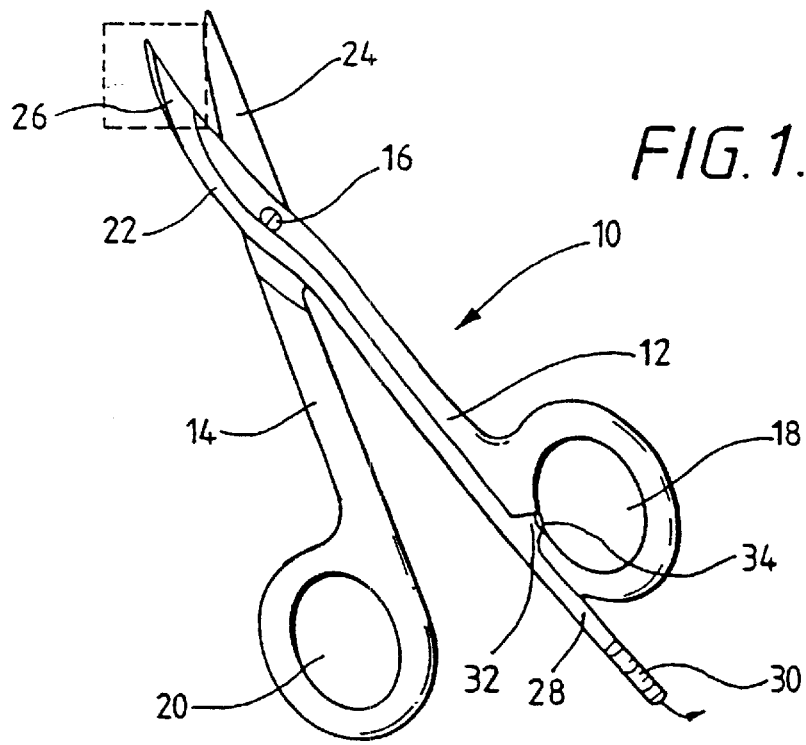
FIG. 1 shows a pair of surgical scissors according to the invention.
Figure 2:
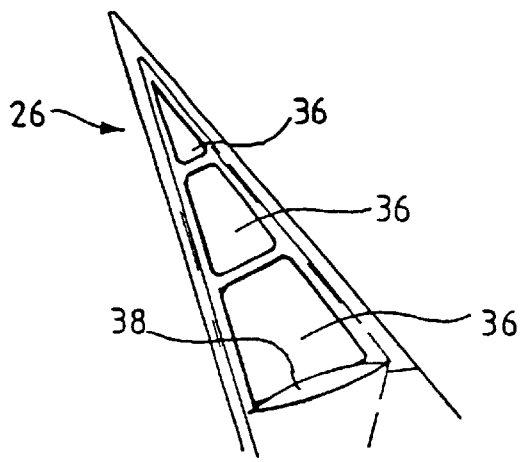
FIG. 2 shows a view on an enlarged scale of the tip of one type of blade which may be used in the scissors of FIG. 1.
Figure 3:
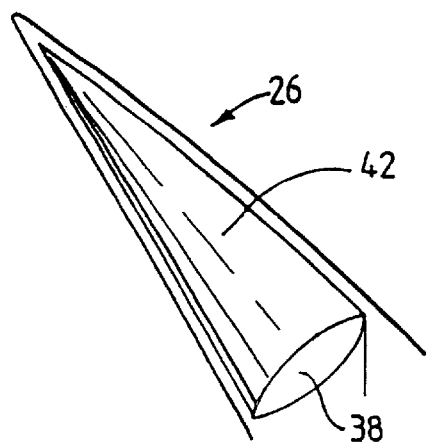
FIG. 3 shows an alternative type of tip for use in the scissors of FIG. 1.

Referring to the embodiment of the invention shown in FIGS. 1 to 3, this is in the form of pair of surgical scissors 10 having members 12 and 14 which are connected by a pivot 16 and which have finger openings 18 and 20 respectively and blades 22 and 24 respectively.

The blade 24 can be conventional in construction, but the blade 22 has a tip portion 26 which is modified for the purposes of the present invention. One form of modified tip is shown on an enlarged scale in FIG. 2, and an alternative form of tip is shown on a similar scale in FIG. 3. The scissors are curved, as are the other embodiments of scissors described herein, and where any of the scissors are shown in plan view they are shown with the concave side facing the viewer. Alternatively, however, the invention, in its various aspects described herein, can be applied to scissors which are straight.

A suction tube 28, which is preferably of metal, though is could be of some other material, runs up one edge of the member 12. The tube may be an entity distinct from the member 12 and merely attached thereto, but it is preferably a tube which is implanted in the member 12. Such implantation could be achieved, for example, by forming a bore in the member 12 and inserting the tube lengthwise in it, or forming a recess in the back edge of the member 12 and inserting the tube into that. In the latter case the exposed portion of the tube might be covered, for example by solder material. A further possibility would be not to have a separate tube 28 as such and rely on a bore in the member 12 to achieve the same effect. For simplicity of description, such as bore is regarded in the ensuing description as itself constituting a tube.

One end of the tube is attached to a flexible tube 30 which in turn is connected to a source of suction (not shown). The other end of the tube terminates in the tip 26, as is described below. The tube 28 has a short branch 32 which communicates with atmosphere via an orifice 34 located in the finger opening 18. The orifice 34 allows a small amount of air to enter the tube 28, and thus, when it is open, reduces the suction effect applied at the tip 26. The surgeon can thus control the amount of applied suction by closing the orifice 34, or opening it wholly or partially, using that one of his fingers which is in the finger hole 18 (this being, under normal circumstances, the surgeon's thumb).

In the embodiment of tip shown in FIG. 2, at least one aperture 36 (three such apertures are shown, though there could be a greater or lesser number) extends through the blade from one face to the other. The upstream end 38 of the suction tube 28 is positioned adjacent one edge of the largest of the three apertures. The tip shown in FIG. 2 provides a significant suction effect only when the scissors are at least partially closed, and control of the suction effect can therefore be achieved by opening and closing the scissors. Additional control, when the scissors are at least partially opened, can be achieved by opening and closing the orifice 34.

In the embodiment of tip shown in FIG. 3, a part-conical depression 42 is formed in that surface of the tip 26 which faces towards the viewer as seen in FIGS. 1 and 3, i.e. the surface which faces away from the blade 24. Suction is here controlled solely by means of the orifice 34.

Two further embodiments of the invention will now be described with reference to FIGS. 4, 5 and 6. In FIG. 4, a pair of surgical scissors is denoted as having a blade 101 and a blade 102, with the cutting surfaces of the blades being denoted below using a suffix C (1C is the cutting surface of blade 101 and 2C is the cutting surface of blade 102), and exterior surfaces of the blades (i.e those which face away from one another) being denoted by the suffix E (with 1E denoting the exterior surface of blade 101 and 2E denoting the exterior surface of blade 102).

FIGS. 5a to 5d show one possible combination of these four surfaces. Surface 2C shown in FIG. 5a has a part-conical recess 50, the larger end of which communicates with the upstream end 38 of the suction tube 28. From this it will be understood that in this embodiment the suction tube is provided in the blade 102. This can be seen more clearly in FIG. 5c, which shows surface 2E. The surface 1C of blade 101 has a part-conical recess 52 which matches the recess 50 in surface 2C, except at the distal end, where a triangular aperture 54 extends through the blade and is thus visible also on surface 1E (see FIG. 5b). Suction is applied by the scissors to the operating site via the aperture 54 when the scissors are at least substantially closed. When they are open it is applied via the grooves 50 and 52.

FIGS. 6a to 6d show an alternative set of surfaces which can be used. In this embodiment, the suction tube 28 is provided on blade 101, with its upstream end 38 opening into surface 1C shown in FIG. 6d. This has the consequence that surface 2E is a regular blade surface, without any additional features resulting from the application of the present invention.

Of course, a further simplification could be achieved by providing a recess in the cutting surface of only one of the blades.

FIGS. 7a to 7d show how a pair of surgical scissors may be provided with means for clamping the patient's tissue. For simplicity, FIGS. 7a to 7d do not show any means for providing the scissors with suction. It is to be understood, however, that such suction means could be provided in the structure shown in FIGS. 7a to 7d, though suction means need not provided.

The scissors of FIGS. 7a to 7d are shown as having a pair of blades 201 and 202, with the tip of blade 202 having a clamp member 204 which, as considered in the view of FIGS. 7c and 7d, overlaps the tip of the blade 201. The blade 201 has, at its tip, a portion which is cut away to define a recess with which the clamp portion 204 can mate, so that when the scissors are closed the face 206 which is thus formed on the blade 201, and which is visible in FIG. 7d, bears against that face of clamp portion 204 which, as viewed in FIG. 7d, is remote from the viewer.

FIG. 8 shows the provision of a pair of surgical scissors with a cautery for effecting cauterization. One terminal (it is illustrated as being the positive terminal, but it could alternatively be the negative terminal) of an electrical supply is connected to a wire 304 which runs along one of the members 301 constituting the scissors (the other of the members is denoted by reference numeral 302) and terminates in a tip portion 306 which is electrically isolated, for example by ceramic insulation material, from the remainder of the member 301.

Figure 18A:
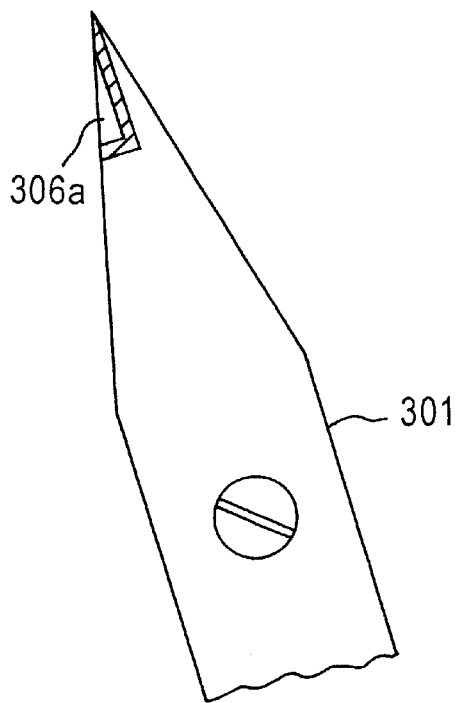
FIGS. 18a and 18b are diagrammatic views of two tip designs for use in providing a bipolar cautery.
Figure 18B:
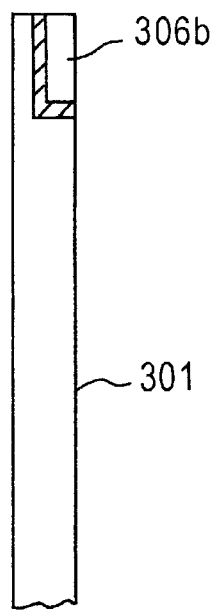

It will further be appreciated that the portion 306 which is electrically isolated from the remainder of the member 301 need not be at the extremity of the member, and could be at some other site located distally of the pivot 16. Also, it could be at the extremity of the member 301 but form only part of the extremity. For example, the isolated portion could be on one face of the member 301 only either the cutting face or the outer face (see the isolated portion 306b in FIG. 18b, which is an enlarged longitudinal section through part of the member 301, taken on a line perpendicular to the plane of the blade). Alternatively, the isolated portion could occupy only one edge portion of the extremity of the member, as seen in plan view, either the cutting edge or the rear edge (see the isolated portion 306a in FIG. 18a, which is a plan view of part of the member 301). In each of FIGS. 18a and 18b the shaped area represents insulation material.

It is also be to be noted that the electrical characteristics of the scissors can be influenced by selecting a given thickness for the insulation material which separates the isolated portion from the remainder. The thinner the insulation material the greater the tendency of the electric current to flow between the isolated portion and the remainder of the member (via the patient's tissue and body fluid), rather than between the isolated portion and the other member 302. Only when the members 301 and 302 are very close to one another will the current flow between them. Conversely when the insulation material is thicker there is greater tendency for current to flow between the isolated portion and the other member, and it will only not do so if the two members are relatively far apart.

It will be understood that the wire 304 is insulated from the member 301 except where it is in electrical contact with the tip portion 306. The other wire 308 is electrically connected directly to the member 301, and indirectly to the member 302 through the pivot 16. A bipolar cautery is thus formed. If a unipolar cautery were desired, one of the wires 304 and 308 would be omitted, and the other connection would be made to the patient's body. For ease of illustration FIG. 8 does not show any means for providing suction to the scissors. It is to be understood, however, that such suction means might be provided, though they need not be. It is also to be understood that the cautery arrangement of FIG. 8 could be combined with the clamp arrangement of FIGS. 7a to 7d, with or without a suction arrangement.

Figure 9:
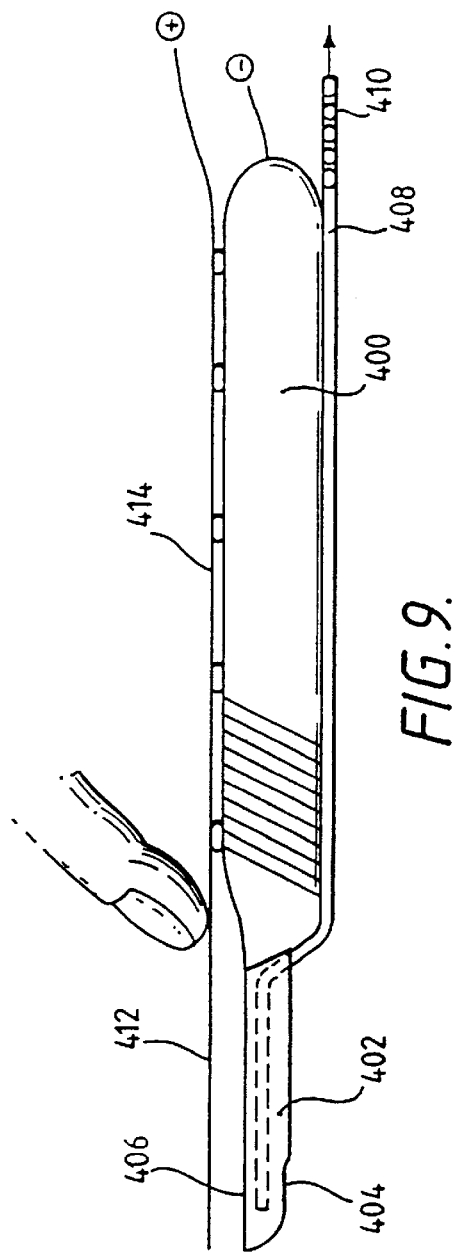
FIG. 9 is a side view of a scalpel according to the present invention, incorporating both suction and cauterization means.
Figure 10:
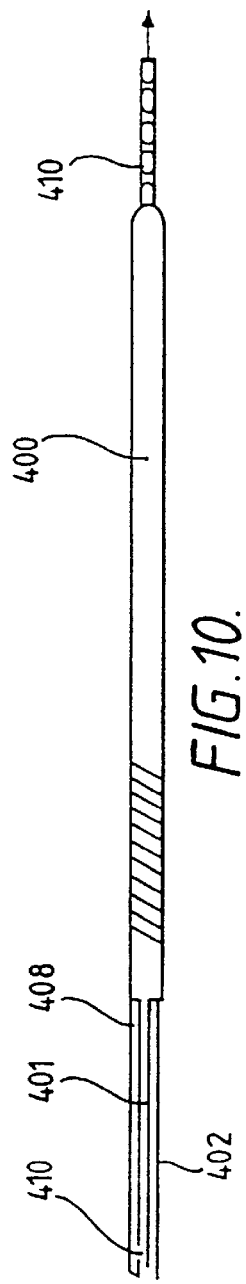
FIG. 10 is a view taken at right angles to FIG. 9, from the dorsal aspect of the scalpel showing the same scalpel, but with a forceps tip and metallic extension thereof omitted for clarity.

FIGS. 9 and 10 illustrate an embodiment of the invention in the form of a scalpel. This is provided both with means for providing suction, with clamping means, and with a cautery. The scalpel comprises a handle 400 having blade holder 401 which carries a blade 402. The blade has a cutting edge 404 and non-cutting edge 406. A suction tube 408 runs along the lower edge of the handle, and thence along one face of the blade 402, to terminate in a suction tip 410. The suction tip faces towards the adjacent face of the blade 402, as can be seen in FIG. 10. The downstream end of the tube 408 is connected to a flexible tube 410 which, in turn, is connected to a source of suction (not shown).

A forceps tip 412 is positioned above, but normally spaced from, the non-cutting edge 406 of the blade 402. The forceps tip 412 is electrically isolated from the handle 400, on which it is mounted. The forceps tip is made of a flexible material, for example spring steel, and can thus be pressed resiliently towards the edge 406, to clamp tissue, for example a piece of tissue which is bleeding, between the forceps tip and the edge 406. The forceps tip 412 is connected via a metallic extension 414 (which is electrically isolated from the handle 400) to one pole of an electrical supply (here shown as the positive pole). The handle 400, and hence the blade 402, is connected to the other pole, here shown as the negative pole. Accordingly, when bleeding tissue is clamped, as described above, it is subjected to a cauterizing action by the electrical current which passes through it, being clamped while cauterization is taking place.

FIGS. 9 and 10 illustrate a bipolar cautery, but a unipolar cautery could be produced by omitting one or other of the electrical connections, and making that connection to the patient's body.

Figure 11:
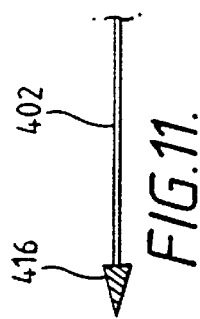
FIG. 11 illustrates a modified scalpel blade, seen from the non-cutting edge thereof.
Figure 14:
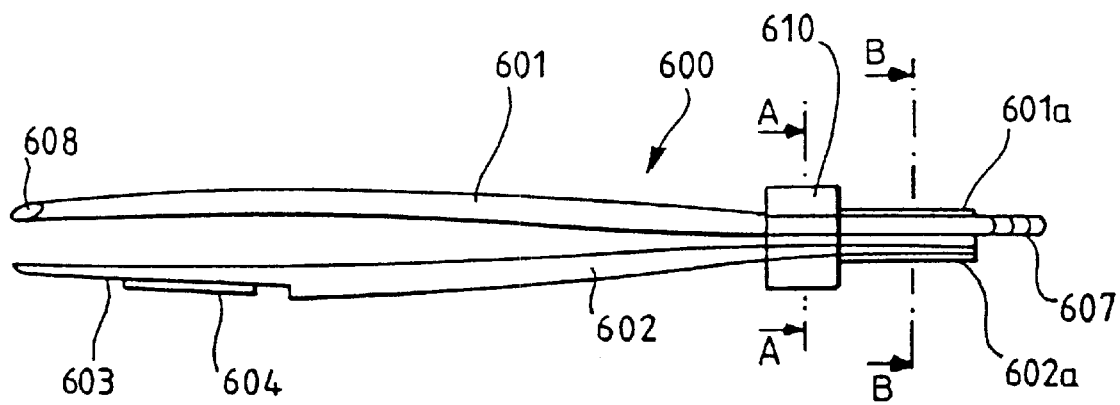
FIG. 14 shows a further embodiment in the form of a pair of forceps provided with a blade holder.
Figure 14A:
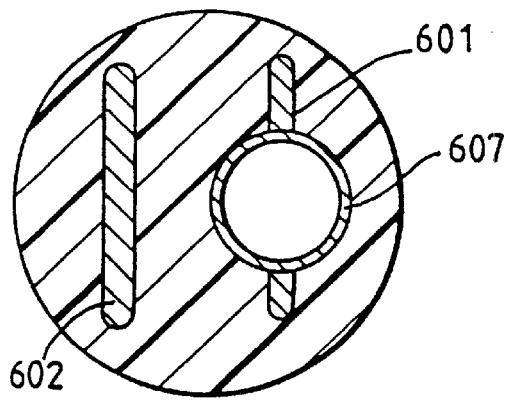
FIGS. 14a and 14b are cross sections through the forceps of FIG. 14, on a larger scale, taken on lines A—A and B—B respectively.
Figure 14B:
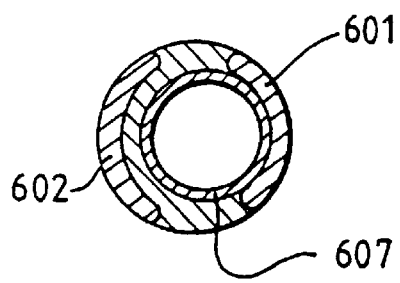
Figure 15:
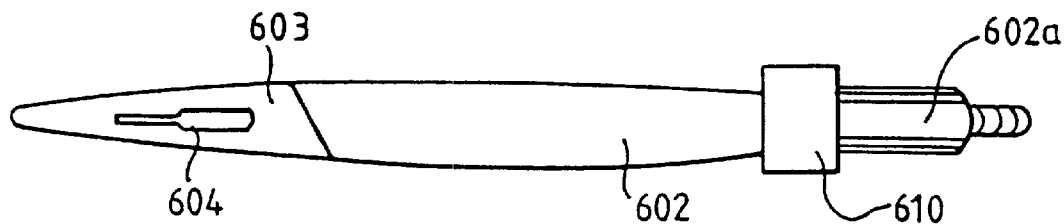
FIG. 15 shows the forceps of FIG. 14 in a view taken at right angles thereto.

FIG. 11 illustrates a modified scalpel blade, in which the tip thereof has a triangular piece 416 formed thereon. The piece 416 can be a separate item which is secured to the blade by suitable means, or it can be formed integrally therewith in the course of manufacture of the blade. The forceps tip preferably has a triangular piece formed at its distal end which is identical in shape and size to the triangular piece 416 formed on the blade.

FIGS. 12 and 13 show a combined suction/cautery unit 500. This comprises a suction tube 502 made, for example, from metal or a plastics material, to which is secured a forceps member 504 made of metal. The forceps member 504 is resiliently flexible and can be urged towards the tube 502. One terminal 506 of an electrical power supply is electrically connected to the forceps member 504. The other pole is connected to the suction tube 502 is the latter is of conductive material (in which case the tube and forceps member must be electrically isolated from one another) or, if the tube is not of conductive material, a conductive wire extends through the tube from the pole, to emerge at the tube exit 510. The other end of the tube 502 is connected to a suction source (not shown).

A plurality of U-shaped guides 512 extend from the tube 502 in a direction away from the forceps member 504. The guides are aligned with one another, and define aligned openings 514 in which a surgical scalpel (not shown) can be received, preferably so as to be removable. In this way the surgeon has the option of using the scalpel alone, or combined with the suction and/or cautery unit, depending on the particular operation. Alternatively, the suction/cautery unit can be used without the scalpel. The suction/cautery unit is sufficiently simple that it should be economical for it to be manufactured, if desired, as a disposable item.

The embodiment of FIGS. 14 to 17 is in the form of forceps 600 comprising first and second forceps arms 601 and 602 which are movable resiliently towards one another. A catch (not shown) may be provided to enable the arms to be releasably held in a position in which they are relatively close to another. The second forceps arm 602 has a recessed area 603 on the outside face thereof, in which is mounted a blade holder 604. This is of a shape to be received in a slot 605 of a surgical blade 606, whereby the blade is fixedly mounted on the outside face of the arm 602.

The forceps arm 601 is provided with a suction tube 607 formed or implanted therein, which can be connected at the proximal end to a source of reduced pressure and which terminates at the distal end in an open tip 608.

The proximal end of the forceps carries an arm housing 610 made of plastics or other insulating material. (The housing 610 is drawn as though it were transparent, so that the structures within it are visible). The forceps arms 601 and 602 are held therein in fixed position and in electrical isolation from one another. Portions 601a and 602a are exposed for electrical connection to respective poles of a bipolar electrical power supply which enables the distal tips of the forceps members to act as a cautery. Alternatively, only one of the forceps arms would have an electrical connection made to it, for use in unipolar cauterisation.

The embodiment of FIGS. 14 to 17 can thus be used as a pair of forceps and as a cutting tool, to which both suction and cauterisation can be applied. When used as a cutting tool they are normally held together by the catch mentioned above. If in any particular situation it is desired not to use its cutting function the blade 606 can simply be omitted.

It should be noted that various of the features described above may be used without a means for applying suction being provided. For example, the surgical cutting tool may be provided with the clamping and/or cauterisation features without suction, and a combined forceps/scalpel unit may be provided without suction. Also, the suction and clamping features may be combined in a tool which is not a cutting tool, i.e. as in FIGS. 12 and 13, but without the scalpel guide means.

I claim:

1. A pair of surgical scissors comprising:

first and second blades each having a cutting surface and an exterior surface, the cutting surfaces facing one another, the blades being pivotally connected one another for relative pivotal movement about a pivotal axis, one of the blades having a blade portion located distally of the pivot axis and electrically insulated from the remainder of said one blade, a first electrical conductor electrically connected to the distal said blade portion, and a second electrical conductor in electrical connection with the remainder of said one blade and with the other blade, thereby enabling the scissors to act as a cautery.

2. A pair of surgical scissors according to claim 1, wherein the said blade portion is at the distal extremity of the blade in which it is located.

3. A pair of surgical scissors according to claim 1, wherein the said blade portion is located only on one edge of the blade in which it is located.

4. A pair of surgical scissors according to claim 1, wherein said blade portion is remote from a cutting edge of the blade in which the blade portion is situated.

5. A pair of surgical scissors, comprising:

first and second blades each having a cutting surface and an exterior surface, the cutting surfaces facing one another, the blades being pivotally connected one another for relative pivotal movement about a pivotal axis, a single one of the blades having a single blade portion located distally of the pivot axis and electrically insulated from the remainder of the blade, a first electrical conductor electrically connected to the distal said blade portion, and a second electrical conductor in electrical connection with the remainder of said one blade and with the other blade, thereby enabling the scissors to act as a cautery, and wherein the said blade portion is located only on one face of the blade in which it is located.

6. A pair of surgical scissors according to claim 5, wherein said blade portion is remote from a cutting edge of the blade in which the blade portion is situated.

7. A pair of surgical scissors comprising:

first and second blades each having a cutting surface and an exterior surface, the cutting surfaces facing one another, the blades being pivotally connected one another for relative pivotal movement about a pivotal axis, one of the blades having a blade portion located distally of the pivot axis and electrically insulated from the remainder of said one blade, a first electrical conductor electrically connected to the distal said blade portion, and a second electrical conductor electrically connected to said one blade, thereby enabling the scissors to act as a cautery at least between said blade portion and the remainder of said one blade.

8. A pair of surgical scissors according to claim 7, wherein said blade portion is remote from a cutting edge of the blade in which the blade portion is situated.

9. A pair of surgical scissors, comprising:

first and second blades each having a cutting surface and an exterior surface, the cutting surfaces facing one another, the blades being pivotally connected one another for relative pivotal movement about a pivotal axis, a single one of the blades having a single blade portion located distally of the pivot axis and electrically insulated from the remainder of the blade, a first electrical conductor electrically connected to the distal blade portion, and a second electrical conductor electrically connected to said one blade, thereby enabling the scissors to act as a cautery at least between said blade portion and the remainder of said one blade, and wherein the said blade portion is located only on one face of the blade in which it is located.

10. A pair of surgical scissors according to claim 9, wherein said blade portion is remote from a cutting edge of the blade in which the blade portion is situated.

* * * * *